US012597144B2

(12) United States Patent
Honda et al.

(10) Patent No.: US 12,597,144 B2
(45) Date of Patent: Apr. 7, 2026

(54) ANTERIOR SEGMENT ANALYSIS APPARATUS, ANTERIOR SEGMENT ANALYSIS METHOD, AND NON-TRANSITORY COMPUTER-READABLE STORAGE MEDIUM

(71) Applicant: TOPCON CORPORATION, Tokyo (JP)

(72) Inventors: Shigeru Honda, Tokyo (JP); Kazunori Asanuma, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 265 days.

(21) Appl. No.: 18/423,609

(22) Filed: Jan. 26, 2024

(65) Prior Publication Data

US 2024/0169547 A1 May 23, 2024

Related U.S. Application Data

(63) Continuation of application No. PCT/JP2022/028662, filed on Jul. 25, 2022.

(30) Foreign Application Priority Data

Jul. 26, 2021 (JP) ................................. 2021-121653

(51) Int. Cl.
*G06K 9/00* (2022.01)
*A61B 3/10* (2006.01)
(Continued)

(52) U.S. Cl.
CPC ................ *G06T 7/12* (2017.01); *A61B 3/102* (2013.01); *A61B 3/117* (2013.01); *G06T 7/0012* (2013.01);
(Continued)

(58) Field of Classification Search
CPC . G06T 2207/30041; G06T 2207/10101; G06T 7/0012; G06T 7/12;
(Continued)

(56) References Cited

U.S. PATENT DOCUMENTS

| | | | | |
|---|---|---|---|---|
| 8,086,063 B2 * | 12/2011 | Aiso | ...................... | H04N 23/63 |
| | | | | 348/222.1 |
| 9,392,936 B1 * | 7/2016 | Yu | .............................. | G06T 5/50 |

(Continued)

FOREIGN PATENT DOCUMENTS

| | | |
|---|---|---|
| JP | 2011-189113 A | 9/2011 |
| JP | 2013-248376 A | 12/2013 |

(Continued)

OTHER PUBLICATIONS

International Search Report mailed on Oct. 11, 2022 in corresponding in PCT Application No. PCT/JP2022/028662, 11 pages.

(Continued)

*Primary Examiner* — Alex Kok S Liew
(74) *Attorney, Agent, or Firm* — XSENSUS LLP

(57) ABSTRACT

An anterior segment analysis apparatus includes a control device configured to: obtain a tomographic image of an anterior segment including a cornea of a subject eye formed by OCT measurement; detect a plurality of edges included in the tomographic image; perform a first joining including joining between edges for each of the plurality of edges based on a first joining condition; select a first edge and a second edge from among the joined edges based on a length; performs a second joining including joining between edges with reference to each of the first edge and the second edge based on a second joining condition; and determine a boundary of a layer of the cornea of the tomographic image using the edges joined by the second joining.

13 Claims, 15 Drawing Sheets

(51) Int. Cl.
*A61B 3/117* (2006.01)
*G06T 7/00* (2017.01)
*G06T 7/12* (2017.01)

(52) U.S. Cl.
CPC ............... *G06T 2207/10101* (2013.01); *G06T 2207/30041* (2013.01)

(58) Field of Classification Search
CPC . G06T 2207/20081; G06T 7/11; G06T 7/162; G06T 2207/10004; G06T 2207/20021; G06T 2207/20076; G06T 7/143; G06T 2207/20084; G06T 7/13; G06T 2200/04; G06T 2200/24; G06T 2207/10048; G06T 7/181; G06T 2207/10064; G06T 2207/30101; G06T 7/0014; G06T 2207/30168; G06T 7/136; G06T 2207/10056; G06T 2207/10072; G06T 2207/20072; G06T 3/00; G06T 7/33; G06T 2207/30096; G06T 5/92; A61B 3/102; A61B 3/0025; A61B 5/0066; A61B 3/14; A61B 2576/02; A61B 5/7203; A61B 3/12; A61B 3/1225
See application file for complete search history.

(56) References Cited

U.S. PATENT DOCUMENTS

| | | | | |
|---|---|---|---|---|
| 10,169,864 | B1 * | 1/2019 | Bagherinia | ............. G06T 7/181 |
| 2011/0200242 | A1 | 8/2011 | Takama et al. | |
| 2011/0243415 | A1 * | 10/2011 | Yonezawa | ................. G06T 7/12 |
| | | | | 382/131 |
| 2012/0140174 | A1 | 6/2012 | Hee et al. | |
| 2013/0208240 | A1 | 8/2013 | Sharma et al. | |
| 2014/0233823 | A1 | 8/2014 | Takama et al. | |
| 2015/0085252 | A1 | 3/2015 | Fujimura et al. | |
| 2015/0085294 | A1 | 3/2015 | Wang et al. | |
| 2015/0092160 | A1 | 4/2015 | Chen et al. | |
| 2016/0317012 | A1 | 11/2016 | Bagherinia | |
| 2016/0345822 | A1 | 12/2016 | Fujimura et al. | |
| 2017/0245756 | A1 | 8/2017 | Hayashi et al. | |
| 2017/0286771 | A1 | 10/2017 | Ishii et al. | |
| 2018/0303334 | A1 | 10/2018 | Tokuyama et al. | |

FOREIGN PATENT DOCUMENTS

| | | |
|---|---|---|
| JP | 2014-500096 A | 1/2014 |
| JP | 2015-506772 A | 3/2015 |
| JP | 2015-066084 A | 4/2015 |
| JP | 2016-077774 A | 5/2016 |
| JP | 2017-182739 A | 10/2017 |
| JP | 6580448 B2 | 9/2019 |
| JP | 2020-048857 A | 4/2020 |
| JP | 2020-199106 A | 12/2020 |

OTHER PUBLICATIONS

Extended European Search Report issued on Jun. 11, 2025 in the corresponding European patent application 22849446.4, 7pp.

* cited by examiner

ANTERIOR SEGMENT ANALYSIS APPARATUS, ANTERIOR SEGMENT ANALYSIS METHOD, AND NON-TRANSITORY COMPUTER-READABLE STORAGE MEDIUM

CROSS-REFERENCE TO RELATED APPLICATION

This is a continuation application of International Application No. PCT/JP20 PCT/JP2022/028662 filed on Jul. 25, 2022 which claims priority from Japanese Patent Application No. 2021-121653 filed on Jul. 26, 2021. The entire contents of the earlier applications are incorporated herein by reference.

TECHNICAL FIELD

The present disclosure relates to an anterior segment analysis apparatus, an anterior segment analysis method, and a program.

BACKGROUND

In the ophthalmic field, there has been an ophthalmic apparatus called OCT (optical coherence tomography). OCT can obtain a tomographic image, an en-face image, a three-dimensional image, or the like of the fundus or the anterior segment of the subject eye. Further, the data obtained by OCT is used for analysis for grasping the state of the subject eye.

For example, JP2020-199106A describes a method of obtaining the shape of the tissue of the subject eye by performing segmentation on a tomographic image of the subject eye. JP2020-48857A describes a method of obtaining the shape of the inner surface of the eye as the object assuming that the eye moves or rotates. Further, Japanese Patent No. 6580448 discloses an ophthalmic information processing apparatus for generating an analysis map of the thickness of the layered tissue of the eye.

SUMMARY

Illustrative aspects of the present disclosure allow appropriate segmentation of local unevenness of a layer constituting the cornea in a tomographic image of the anterior segment.

In order to solve the above problems, one illustrative embodiment of the present disclosure has the following configuration. That is, an anterior segment analysis apparatus includes a control device configured to:

obtain a tomographic image of an anterior segment including a cornea of a subject eye formed by OCT measurement;

detect a plurality of edges included in the tomographic image;

perform a first joining including joining between edges for each of the plurality of edges based on a first joining condition;

select a first edge and a second edge from among the edges joined by the first joining based on a length;

perform a second joining including joining between edges with reference to each of the first edge and the second edge based on a second joining condition; and determine a boundary of a layer of the cornea of the tomographic image using the edges joined by the second joining.

Another illustrative embodiment of the present disclosure has the following configuration. That is, an anterior segment analysis method includes:

obtaining a tomographic image of an anterior segment including a cornea of a subject eye formed by OCT measurement;

detecting a plurality of edges included in the tomographic image;

performing a first joining including joining between edges for each of the plurality of edges based on a first joining condition;

selecting a first edge and a second edge from among the edges joined by the first joining based on a length;

performing a second joining including joining between edges with reference to each of the first edge and the second edge based on a second joining condition; and determining a boundary of a layer of the cornea of the tomographic image using the edges joined by the second joining.

Still another illustrative embodiment of the present disclosure has the following configuration. That is, a non-transitory computer-readable storage medium storing a computer program readable by a computer, the computer program, when executed by the computer, causes the computer to perform operations including:

obtaining a tomographic image of an anterior segment including a cornea of a subject eye formed by OCT measurement;

detecting a plurality of edges included in the tomographic image;

performing a first joining including joining between edges for each of the plurality of edges based on a first joining condition;

selecting a first edge and a second edge from among the edges joined by the first joining based on a length;

performing a second joining including joining between edges with reference to each of the first edge and the second edge based on a second joining condition; and determining a boundary of a layer of the cornea of the anterior segment using the edges joined by the second joining.

According to the present disclosure, it is possible to allow appropriate segmentation on local unevenness of a layer constituting the cornea in the anterior segment.

BRIEF DESCRIPTION OF DRAWINGS

Illustrative aspects of the disclosure are illustrated by way of example and not by limitation in the accompanying figures in which like reference characters indicate similar elements.

DETAILED DESCRIPTION

Figure 1:
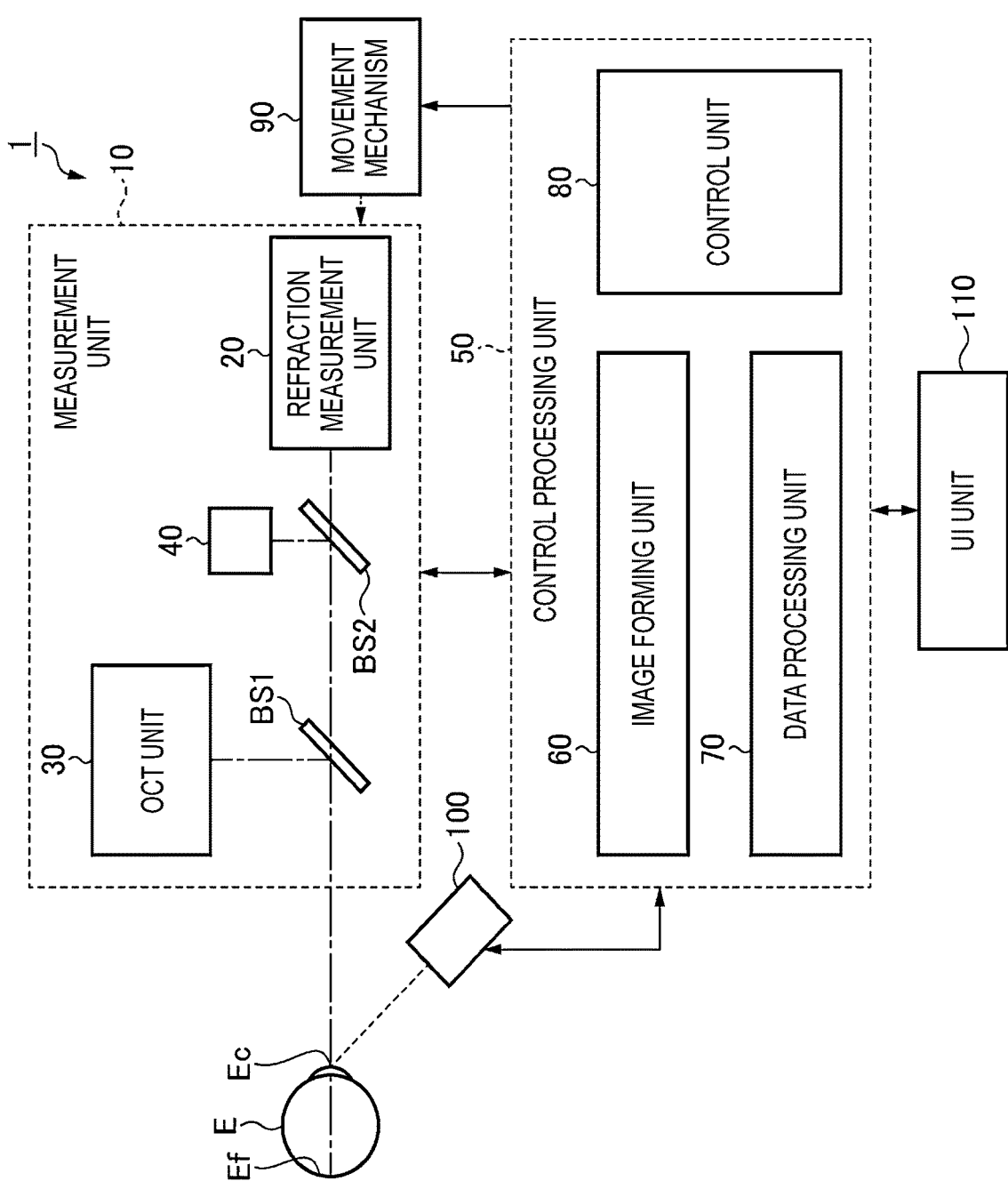
FIG. 1 is a functional configuration diagram illustrating an example of a system configuration according to an illustrative embodiment of the present disclosure.

In OCT, it is conceivable to obtain a tomographic image of the anterior segment or the fundus of the subject eye. Among these, the boundary of the fundus layer can be imaged relatively clearly, which allows easy segmentation, that is, separation into a single layer from the image. On the other hand, the anterior segment is difficult to clearly image in the imaging operation, and thus is difficult to segment from the image.

For example, in the technique in the related art as disclosed in JP2020-48857A, in the segmentation of the cornea positioned in the anterior segment, the noise of the OCT image and the Bowman's layer, which is an inter-tissue layer, have low contrast, and thus the shape of the Bowman's membrane is obtained by polynomial approximation. However, this method cannot appropriately segment a locally uneven layer in the cornea located in the anterior segment of the patient's eye.

Therefore, illustrative aspects of the present disclosure allow appropriate segmentation of local unevenness of a layer constituting the cornea in a tomographic image of the anterior segment.

Illustrative embodiments of an anterior segment analysis apparatus, an anterior segment analysis method, and a program according to the present disclosure will be described in detail with reference to the drawings. The description contents of the documents cited in this specification and any known technique can be applied to the following illustrative embodiments. The illustrative embodiment described below is an illustrative embodiment for describing the present invention and is not intended to be interpreted to limit the present invention. Not all the configurations described in the illustrative embodiments are necessarily essential to solve the problem of the present invention. In the drawings, the same components are denoted by the same reference numerals to illustrate the correspondence therebetween.

Examples of the tissue in the subject eye include the tissue in the anterior segment and the tissue in the posterior segment. The tissue in the anterior segment includes the cornea, the iris, the lens, the ciliary body, the Zinn's zonule, and the iridocorneal angle. The tissue in the posterior segment includes the fundus (a predetermined layer region in the fundus) and the like. The cornea positioned at the anterior segment of interest in the present disclosure is formed of a plurality of layers. More specifically, the layered structure includes the corneal epithelial cells, the Bowman's membrane, the corneal parenchyma, the Descemet's layer, and the corneal endothelial cells in order from the anterior side of the cornea.

As described above, the boundary of the fundus layer can be imaged relatively clearly, which allows easier separation into a single layer from the image. On the other hand, the anterior segment is difficult to clearly image in the imaging operation, and thus is difficult to separate into the plurality of layers constituting the anterior segment as described above. Hereinafter, the present illustrative embodiment will describe an anterior segment analysis method for more accurately detecting the anterior segment, particularly the layered structure of the cornea.

The anterior segment analysis method according to an illustrative embodiment of the present disclosure obtains and uses a tomographic image of the subject eye. The tomographic image is obtained, for example, by performing optical coherence tomography (OCT) on the subject eye using an external ophthalmic system.

In this specification, the data obtained by OCT may be collectively referred to as OCT data. The measurement operation for forming the OCT data may be referred to as OCT measurement, and the scan for performing OCT measurement may be referred to as OCT scan.

First Illustrative Embodiment

Hereinafter, a case where an ophthalmic system according to the illustrative embodiment of the present disclosure includes an anterior segment analysis apparatus will be described. The ophthalmic system includes an OCT apparatus, and obtains a tomographic image of the subject eye by performing OCT measurement on the subject eye using the OCT apparatus. However, the present disclosure is not limited to this configuration. For example, the anterior segment analysis apparatus may include an interface for transmitting and receiving data from an external apparatus or a recording medium via a network, and may obtain the OCT data, the tomographic image, and the like from an external ophthalmic system.

In the following description, the left-right direction (horizontal direction) orthogonal to the optical axes (measurement optical axis, inspection optical axis) of the apparatus optical system of the ophthalmic system is defined as the X direction, the upper-lower direction (vertical direction) orthogonal to the optical axes is defined as the Y direction, and the direction of the optical axes (depth direction, front-rear direction) is defined as the Z direction. The correspondence relationship between the three-dimensional coordinate system in the real space and the three-dimensional coordinate system inside the system or in the three-dimensional data is not particularly limited, but they are assumed as associated in advanced.

System Structure

FIG. 1 illustrates a configuration example of an ophthalmic system 1 including a function for executing the anterior segment analysis method according to the present illustrative embodiment. Here, a part of the system that can be applied with the anterior segment analysis method according to the present disclosure is illustrated representatively, but the ophthalmic system 1 may further include a configuration other than that illustrated in FIG. 1.

The ophthalmic system 1 is an inspection apparatus including an objective refraction measurement apparatus (refraction measurement unit) and an OCT apparatus (OCT unit). The ophthalmic system 1 includes a measurement unit 10, a control processing unit 50, a movement mechanism 90, an imaging unit 100, and a UI (user interface) unit 110. The measurement unit 10 includes a refraction measurement unit 20, an OCT unit 30, a light projection unit 40, a beam splitter BS1, and a beam splitter BS2. The control processing unit 50 includes an image forming unit 60, a data processing unit 70, and a control unit 80.

{Refraction Measurement Unit}

The refraction measurement unit 20 receives a control instruction from the control unit 80, thereby objectively measuring the refractive power of the subject eye E. The refraction measurement unit 20 includes an optical system provided with one or more optical members for performing objective refraction measurement. The refraction measurement unit has the same configuration as, for example, a known refractometer. Although not illustrated, a typical refractometer includes a projection system and a light reception system as disclosed in JP2016-077774A.

The projection system of the refraction measurement unit 20 projects light emitted from a light source onto a fundus Ef of the subject eye E. For example, the projection system projects light from a light source onto the fundus Ef through a collimator lens, a focusing lens, a relay lens, a pupil lens, a perforated prism, a decentered prism, an objective lens, or the like.

The light reception system of the refraction measurement unit 20 projects the reflected light from the fundus Ef onto an imaging element (not illustrated) through an objective lens, a decentered prism, a perforated prism, another pupil lens, another relay lens, another focusing lens, a conical prism, an image forming lens, or the like. Thus, a ring-pattern image formed on the imaging surface of the imaging element is detected.

The refraction measurement unit 20 may project ring-shaped light onto the fundus Ef and detect a ring-pattern image formed by the reflected light from the fundus Ef. Alternatively, the refraction measurement unit 20 may project a bright spot onto the fundus Ef, convert the reflected light from the fundus Ef into ring-shaped light, and detect a ring-pattern image formed by the converted ring-shaped light.

{OCT Unit}

The OCT unit 30 receives a control instruction from the control unit 80 and applies OCT scan to the subject eye E to obtain OCT data. The OCT data may be interference signal data, reflection intensity profile data obtained by applying Fourier transform to the interference signal data, or image data obtained by imaging the reflection intensity profile data. In the present illustrative embodiment, an example using image data (hereinafter referred to as an OCT image) will be described.

The OCT technique that can be performed by the OCT unit 30 is typically Fourier domain OCT, and may be either spectral domain OCT or swept source OCT. In swept source OCT, light from a variable-wavelength light source is split into the measurement light and the reference light, and the return light of the measurement light projected onto the subject eye is superimposed on the reference light to generate the interference light. Then, the interference light is detected by a photodetector, and the detection data (interference signal data) collected according to the wavelength sweeping and the measurement light scanning is subjected to Fourier transform or the like to form the reflection intensity profile data. On the other hand, in spectral domain OCT, the light from a low-coherence light source (wide-band light source) is split into the measurement light and the reference light, and the return light of the measurement light projected onto the subject eye is superimposed on the reference light to generate the interference light. Then, the spectral distribution of the interference light is detected by a spectrometer, and the detection data (interference signal data) obtained by the spectrometer is subjected to Fourier transform to form the reflection intensity profile data. In other words, swept source OCT is an OCT technique of obtaining a spectral distribution by time division, while spectral domain OCT is an OCT technique of obtaining a spectral distribution by spatial division.

The OCT unit 30 includes an optical system provided with one or more optical members for performing OCT measurement. The OCT unit 30 has, for example, a configuration similar to that of a known OCT apparatus. Although not illustrated, a typical OCT apparatus includes a light source, an interference optical system, a scanning system, and a detection system as disclosed in JP2016-077774A.

The light output from the light source is split into the measurement light and the reference light by the interference optical system. The reference light is guided by a reference arm. The measurement light is projected onto the subject eye E (for example, the fundus Ef) through a measurement arm. The measurement arm is provided with a scanning system. The scanning system includes, for example, an optical scanner, and can deflect the measurement light one-dimensionally or two-dimensionally. The optical scanner includes one or more galvanometer scanners. The scanning system deflects the measurement light in accordance with a predetermined scan mode.

The control unit 80 included in the control processing unit 50 can control the scanning system in accordance with the scan mode. The scan mode includes line scan, raster scan (three-dimensional scan), circle scan, concentric circle scan, radial scan, cross scan, multi-cross scan, spiral scan, and the like. Line scan is a scan pattern along a linear trajectory. Raster scan is a scan pattern including a plurality of line scans arranged in parallel to each other. Circle scan is a scan pattern along a circular trajectory. Concentric circle scan is a scan pattern including a plurality of circle scans arranged concentrically. Radial scan is a scan pattern including a plurality of line scans arranged radially. Cross scan is a scan pattern including two line scans arranged orthogonal to each other. Multi-cross scan is a scan pattern including two line scan groups orthogonal to each other (for example, each group includes five lines parallel to each other). Spiral scan is a scan pattern extending spirally from the center.

The measurement light projected onto the fundus Ef is reflected and scattered at various depth positions (layer boundaries and the like) of the fundus Ef. The return light of the measurement light from the subject eye E is synthesized with the reference light by the interference optical system.

The return light of the measurement light and the reference light generate interference light according to the superposition principle. The interference light is detected by a detection system. The detection system typically includes a spectrometer in spectral domain OCT, and includes a balanced photodiode and a DAQ (data acquisition) system in swept source OCT.

{Light Projection Unit}

The light projection unit 40 projects, onto the subject eye E, light for performing alignment between the subject eye E and the measurement unit 10 (OCT unit 30, apparatus optical system). The light projection unit 40 includes a light source and a collimator lens. The optical path of the light projection unit 40 is joined to the optical path of the refraction measurement unit 20 by the beam splitter B S2. The light output from the light source passes through the collimator lens, is reflected by the beam splitter B S2, and is projected onto the subject eye E through the optical path of the refraction measurement unit 20.

In some illustrative embodiments, as disclosed in JP2016-077774A, the reflected light from the cornea Ec (anterior segment) of the subject eye E is guided to the light reception system of the refraction measurement unit 20 through the optical path of the refraction measurement unit 20.

An image based on the reflected light from the cornea Ec of the subject eye E (bright spot image) is included in an anterior segment image obtained by the imaging unit 100. For example, the control processing unit 50 displays the anterior segment image including the bright spot image and an alignment mark on the display screen of the display unit (not illustrated). To perform alignment in the X and Y directions (alignment in the upper, lower, left, and right directions), the user can move the optical system to guide the bright spot image into the alignment mark. To manually perform alignment in the Z direction (alignment in the front-rear direction), the user can move the optical system while referring to the anterior segment image displayed on the display screen of the UI unit 110. To automatically perform alignment, the control unit 80 moves the measurement unit 10 (optical system) relative to the subject eye E by controlling the movement mechanism 90 to cancel the displacement between the alignment mark and the position of the bright spot image. Alternatively, the control unit 80 can move the measurement unit 10 (optical system) relative to the subject eye E by controlling the movement mechanism 90 to satisfy a predetermined completion condition for alignment based on the position of a predetermined portion of the subject eye E (for example, the pupil center position) and the position of the bright spot image.

{Beam Splitter}

The beam splitter BS1 coaxially joins the optical path of the optical system of the OCT unit 30 (interference optical system or the like) to the optical path of the optical system of the refraction measurement unit 20 (projection system and light reception system). For example, a dichroic mirror is used as the beam splitter BS1. The beam splitter BS2 coaxially joins the optical path of the optical system of the light projection unit 40 to the optical path of the optical system of the refraction measurement unit 20 (projection system and light reception system). For example, a half mirror is used as the beam splitter BS2.

The ophthalmic system 1 may have a function (fixation projection system) of presenting, to the subject eye E, a fixation target for guiding the line of sight of the subject eye E in response to a control instruction from the control unit 80. The fixation target may be an internal fixation target presented to the subject eye E, or may be an external fixation target presented to the fellow eye. The optical path of the fixation projection system may be coaxially joined to the optical path of the interference optical system of the OCT unit 30 by an optical path joining member (for example, a beam splitter) disposed between the OCT unit 30 and the beam splitter BS1.

The projection position of the fixation target on the fundus oculi Ef by the fixation projection system can be changed in response to a control instruction from the control unit 80. The fixation target may be projected on the measurement optical axis of the optical system of the refraction measurement unit 20 and the optical system of the OCT unit 30, which are joined coaxially. The fixation target may be projected on the fundus Ef at a position deviated from the measurement optical axis.

{Imaging Unit}

The imaging unit 100 includes one or more anterior segment cameras for imaging the anterior segment of the subject eye E. The imaging unit 100 obtains an anterior segment image which is an en-face image of the subject eye E. The vicinity of the one or more anterior segment cameras may be provided with at least one anterior segment illumination light source (infrared light source or the like). For example, the upper vicinity and the lower vicinity of each anterior segment camera may be each provided with an anterior segment illumination light source.

The ophthalmic system 1 can align the measurement unit 10 (optical system) with the subject eye E using the en-face image obtained by the imaging unit 100. The ophthalmic system 1 may identify the three-dimensional position of the subject eye E by analyzing the en-face image obtained by imaging the anterior segment of the subject eye E, and perform alignment by relatively moving the measurement unit 10 based on the identified three-dimensional position. The ophthalmic system 1 may perform alignment to cancel the displacement between the feature position of the subject eye E and the position of the image formed by the light projected from the light projection unit 40.

The imaging unit 100 includes one or more anterior segment cameras. If the imaging unit 100 includes a single anterior segment camera, the ophthalmic system 1 analyzes the obtained en-face image to identify the two-dimensional position of the subject eye E on a plane orthogonal to the optical axis of the measurement unit 10 (a plane defined by the horizontal direction (X direction) and the vertical direction (Y direction)). In this case, the ophthalmic system 1 is provided with an optical system for identifying the position of the subject eye E in the direction of the optical axis of the measurement unit 10. Examples of such an optical system include an optical system of the optical lever type as disclosed in JP2016-077774A. The ophthalmic system 1 can use such an optical system to identify the three-dimensional position of the subject eye E based on the position of the subject eye E in the direction of the (measurement) optical axis of the measurement unit 10 and the two-dimensional position described above.

If the imaging unit 100 includes two or more anterior segment cameras, the two or more anterior segment cameras image the anterior segment of the subject eye E from different directions. The two or more anterior segment cameras can substantially simultaneously image the anterior segment from the two or more different directions. "Substantially simultaneously" allows, for example, a deviation in imaging timing to the extent that eye movement can be ignored in imaging with the two or more anterior segment cameras. Accordingly, an image when the subject eye E is at substantially the same position (orientation) can be obtained by the two or more anterior segment cameras. For example, as disclosed in JP2013-248376A, the ophthalmic system 1 analyzes the obtained en-face image to identify the feature position of the subject eye E, and identifies the three-dimensional position of the subject eye E from the positions of two or more anterior segment cameras and the identified feature position of the subject eye E.

The imaging by the two or more anterior segment cameras may be dynamic imaging or still imaging. In the case of dynamic imaging, it is possible to achieve the substantially simultaneous anterior segment imaging as described above by performing control to match the imaging start timings or controlling the frame rate or the imaging timing of each frame. On the other hand, in the case of still imaging, this can be achieved by performing control to match the imaging timings.

{Control Processing Unit}

The control processing unit 50 executes various calculations and various controls for operating the ophthalmic system 1. The control processing unit 50 includes one or more processors and one or more storage devices. Examples of the storage device include a RAM (random access memory), a ROM (read only memory), an HDD (hard disk drive), and an SSD (solid state drive). Various computer programs are stored in the storage device, and calculation and control according to the present illustrative embodiment are achieved by operating the processor based on the computer programs.

In the present illustrative embodiment, the control processing unit 50 achieves the functions of the image forming unit 60, the data processing unit 70, and the control unit 80 by the processor executing various programs. The block configuration of the functions achieved by the control processing unit 50 is an example, and the functions may be further divided in detail corresponding to the respective processes described above.

{Image Forming Unit}

The image forming unit 60 forms an image (tomographic image or the like) of the subject eye E based on the OCT data obtained by performing OCT measurement on the subject eye E. The image forming unit 60 constructs the OCT data (typically, image data) based on the detection data by the detection system of the OCT unit 30. Similarly to the OCT data processing in the related art, the image forming unit 60 applies filtering, FFT (fast Fourier transform), or the like to the detection data, thereby constructing the reflection intensity profile data for each A-line (the path of the measurement light in the subject eye E). Further, the image forming unit 60 applies imaging (image representation) to the reflection intensity profile data to construct the image data of each A-line (A-scan data). A part of the functions of the image forming unit 60 may be provided in the OCT unit 30.

If the apparatus for executing the anterior segment analysis method according to the present illustrative embodiment is achieved as an apparatus separate from the measurement unit 10, the image forming unit 60 may be configured as an obtainment unit for obtaining the OCT data via a network (not illustrated).

{Data Processing Unit}

The data processing unit 70 can execute a process for aligning the measurement unit with respect to the subject eye E. Examples of the process for alignment include analysis of the en-face image of the subject eye E obtained using the imaging unit 100, calculation of the position of the subject eye E, and calculation of the displacement of the measurement unit with respect to the subject eye E.

The data processing unit 70 can perform the OCT measurement after the alignment to identify the surface shape of the cornea Ec of the subject eye E from the tomographic image of the subject eye E obtained, and can further generate shape data representing the structure of the cornea Ec. For example, the shape data is obtained by segmenting the tomographic image as the OCT image. The present illustrative embodiment performs analysis including segmentation for the cornea Ec included in the anterior segment, and performs display based on the analysis result or the like. Details will be described later.

{Control Unit}

The control unit 80 controls each unit of the ophthalmic system 1. The control unit 80 includes a storage device as described above (not illustrated), and can store various information. The information stored in the storage device includes a program for controlling each unit of the ophthalmic system 1, information on the subject, information on the subject eye, the measurement data obtained by the measurement unit 10, and the processing result by the data processing unit 70, but is not particularly limited thereto.

The control unit 80 can control the UI unit 110. The UI unit 110 functions as a part of a user interface, functions as a display device for displaying information or a display screen in response to a control instruction from the control unit 80, and functions as an operation device for receiving an operation from the user. The UI unit 110 may include, for example, an LCD (liquid crystal display) or an OLED (organic light-emitting diode) display to function as a display device.

The control unit 80 can control the ophthalmic system 1 in accordance with a signal input via the UI unit 110. The UI unit 110 may include various hardware keys (a joystick, a button, a switch, or the like) provided in the ophthalmic system 1 to function as an operation device. The UI unit 110 may include various peripheral devices (a keyboard, a mouse, a joystick, an operation panel, or the like) connected to the ophthalmic system 1. The UI unit 110 may include various software keys (a button, an icon, a menu, or the like) displayed on the touch panel.

{Movement Mechanism}

The movement mechanism 90 is a mechanism for moving the measurement unit 10 accommodating the optical systems (apparatus optical systems) such as the refraction measurement unit 20, the OCT unit 30, the light projection unit 40, and the beam splitters B S1 and B S2 in the vertical and horizontal directions and the front-rear direction. The movement mechanism 90 can receive a control instruction from the control unit 80 and move the measurement unit 10 relative to the subject eye E. For example, the movement mechanism 90 is provided with an actuator (not illustrated) for generating a driving force for moving the measurement unit 10 and a transmission mechanism (not illustrated) for transmitting the driving force. The actuator includes, for example, a pulse motor. The transmission mechanism is constituted by, for example, a combination of gears or a rack-and-pinion. The control unit 80 controls the movement mechanism 90 by sending a control signal to the actuator.

The control for the movement mechanism 90 is used for alignment. For example, the control unit 80 obtains the current position of the measurement unit 10 (the apparatus optical system). The control unit 80 receives the information indicating the content of the movement control of the movement mechanism 90 to obtain the current position of the measurement unit 10. In this case, the control unit 80 controls the movement mechanism 90 at a predetermined timing (when the apparatus is activated, when the patient information is input, or the like) to move the measurement unit 10 to a predetermined initial position. Thereafter, the control unit 80 records the control content every time the control unit 80 controls the movement mechanism 90. Thus, the history of the control content is obtained. The control unit 80 serves as an optical system position obtainment unit to obtain the control content up to the present with reference to the history and to obtain the current position of the measurement unit 10 based on the control content.

The control for the movement mechanism 90 may be used for tracking. Tracking is to move the apparatus optical system in accordance with the eye movement of the subject eye E. To perform tracking, alignment and focus adjustment are performed in advance. Tracking is a function for maintaining a suitable position relationship in which the position is in focus by causing the position of the apparatus optical system to follow the eye movement.

Layers of Cornea

Figure 2:
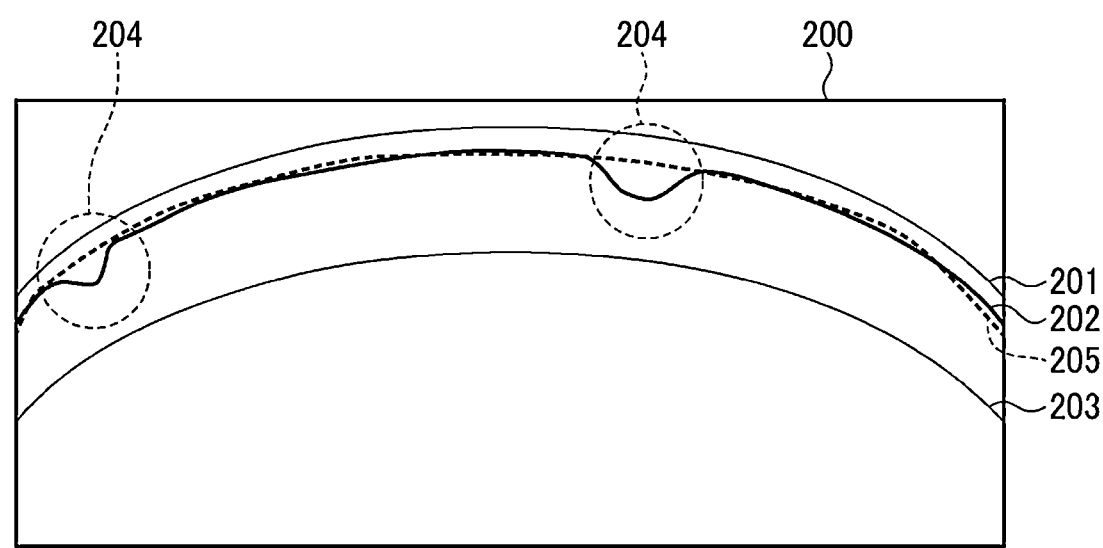
FIG. 2 is a diagram for explaining a detection example of a layer of a cornea in the related art.

As described above, the cornea Ec located at the anterior segment has a layered structure, and includes the corneal epithelial cells, the Bowman's membrane, the corneal parenchyma, the Descemet's layer, and the corneal endothelial cells. FIG. 2 is a diagram for explaining a detection example of the boundary portion of each layer of the cornea in the related art. An image 200 illustrates a part of the cornea, and here illustrates a detection example of a boundary 201 on the anterior side of the corneal epithelium, a boundary 202 between the corneal epithelium and the Bowman's membrane, and a boundary 203 on the fundus side of the corneal endothelium. The thickness of the cornea is about 0.5 mm. Among them, the Bowman's membrane has a thickness of about 8 to 14 μm, and is a layer thinner than the corneal epithelial cells and the corneal parenchyma which are other components.

In the technique in the related art, to detect the boundary 202 between the Bowman's membrane and the corneal epithelium, the detection is performed using an approximative curve as described in, for example, JP2020-48857A. If the boundary is detected using an approximative curve, for example, a curve 205 is obtained as the boundary. If such a detection method is used, it is not possible to accurately detect the unevenness generated in the Bowman's membrane or the like as illustrated in the region 204.

In the anterior segment analysis method according to the present illustrative embodiment, the unevenness generated inside the cornea as described above can also be detected, and more accurate detection is achieved.

Processing Flow

Hereinafter, the process of the anterior segment analysis method according to the illustrative embodiment of the present disclosure will be described. This processing is achieved by, for example, the processor included in the ophthalmic system 1 reading and executing the various programs stored in the storage device and operating as the control processing unit 50.

In step S101, the image forming unit 60 obtains the OCT data of the subject eye to be processed. The OCT data may be newly obtained by imaging the subject eye by operating the measurement unit 10 and the movement mechanism 90 under the control of the control unit 80, or the OCT data held in a storage device or the like may be obtained. Here, the OCT data to be obtained may be designated by the user. At this time, the OCT data may be subjected to pre-processing such as gradation conversion, image enhancement, threshold processing, contrast conversion, binarization, edge detection, image averaging, image smoothing, filtering, region extraction, and alignment. The pre-processing is not limited to the above, and other processes may be performed in consideration of the subsequent processes.

In step S102, the data processing unit 70 detects the boundary on the anterior side of the corneal epithelium by performing edge detection on the OCT data obtained in step S101. The boundary detected here corresponds to the boundary 201 illustrated in FIG. 2. That is, the boundary corresponds to the edge positioned on the most anterior side of the cornea. Examples of the edge detection method include, but are not limited to, the Canny Edge detection, which is a known technique. Further, the data processing unit 70 detects the boundary on the anterior side of the corneal epithelium from the approximative curve based on the detected edges.

In step S103, the data processing unit 70 performs alignment on the original OCT image based on the position of the boundary detected in step S102 so that the boundary becomes a straight line. That is, the pixels constituting the detected boundary are arranged linearly, and the pixels are subjected to position conversion while maintaining the position relationship in a predetermined direction between the pixels constituting the boundary and the other pixels. Accordingly, the position relationship (distance) in the thickness direction between the pixels of the boundary and the surrounding pixels does not change from the original image. By performing such alignment, it is possible to identify a fine structure even in a process requiring accuracy of several such as detecting each layer constituting the cornea.

Figure 4A:
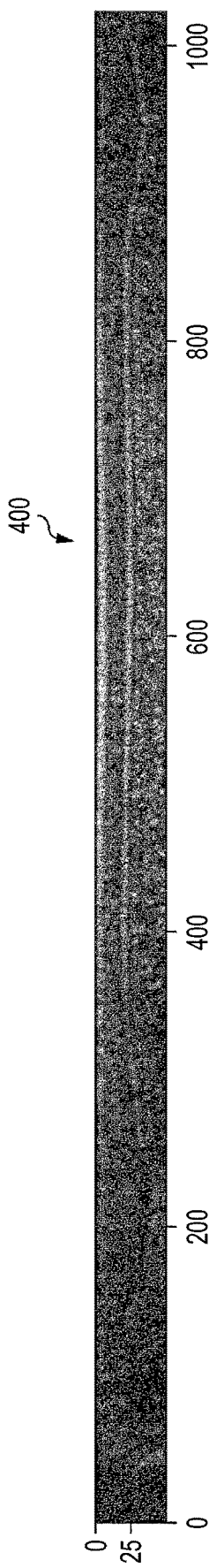
FIG. 4A is a diagram for explaining the transition of an image to be processed according to the illustrative embodiment of the present disclosure.

In step S104, the data processing unit 70 extracts a region of a predetermined size based on the boundary from the image after alignment obtained in step S103. As a result, a rectangular corneal image 401 as illustrated in FIG. 4A is obtained. The predetermined size of the extracted region is not particularly limited, and may be, for example, 50 pixels in the direction orthogonal to the boundary and 1024 pixels in the direction parallel to the boundary. The upper end in the vertical direction corresponds to the straight line obtained at the boundary detected in step S102.

Figure 5:
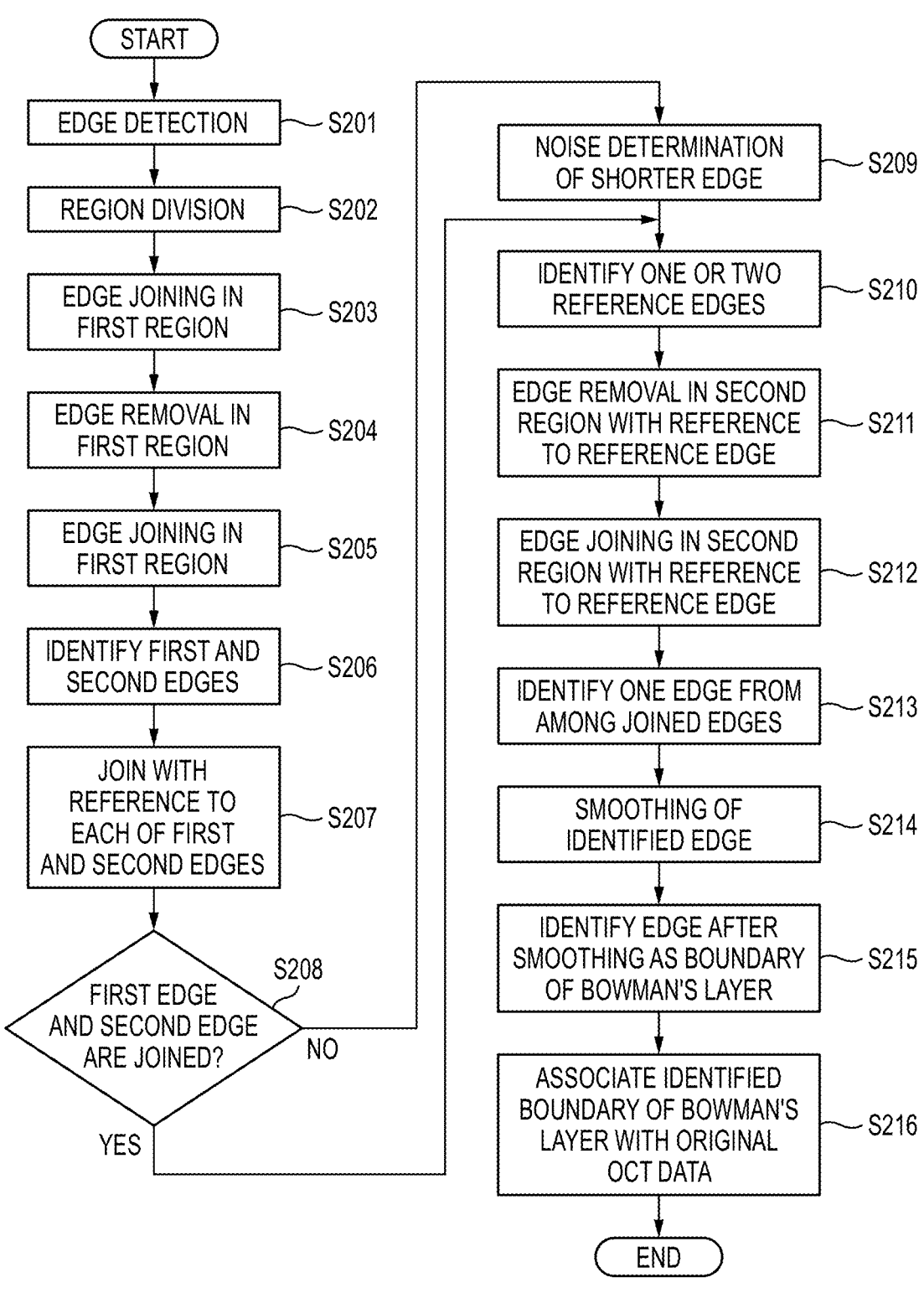
FIG. 5 is a flowchart for identifying the boundary of the Bowman's membrane according to the illustrative embodiment of the present disclosure.

In step S105, the data processing unit 70 performs a process of identifying the boundary of the Bowman's membrane using the corneal image obtained in step S104. This step will be described in detail with reference to FIG. 5.

In step S106, the data processing unit 70 performs display based on the boundary of the Bowman's membrane identified in step S105. A configuration example of a screen displayed on the UI unit 110 in the display will be described later. Then, this processing flow ends.

{Process of Identifying Boundary of Bowman's Membrane}

Figure 3:
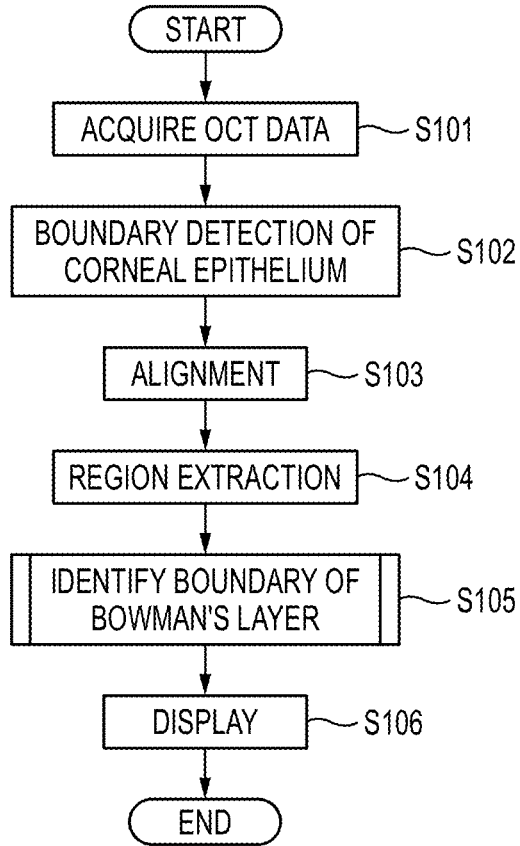
FIG. 3 is a flowchart of an anterior segment analysis according to the illustrative embodiment of the present disclosure.
Figure 6:
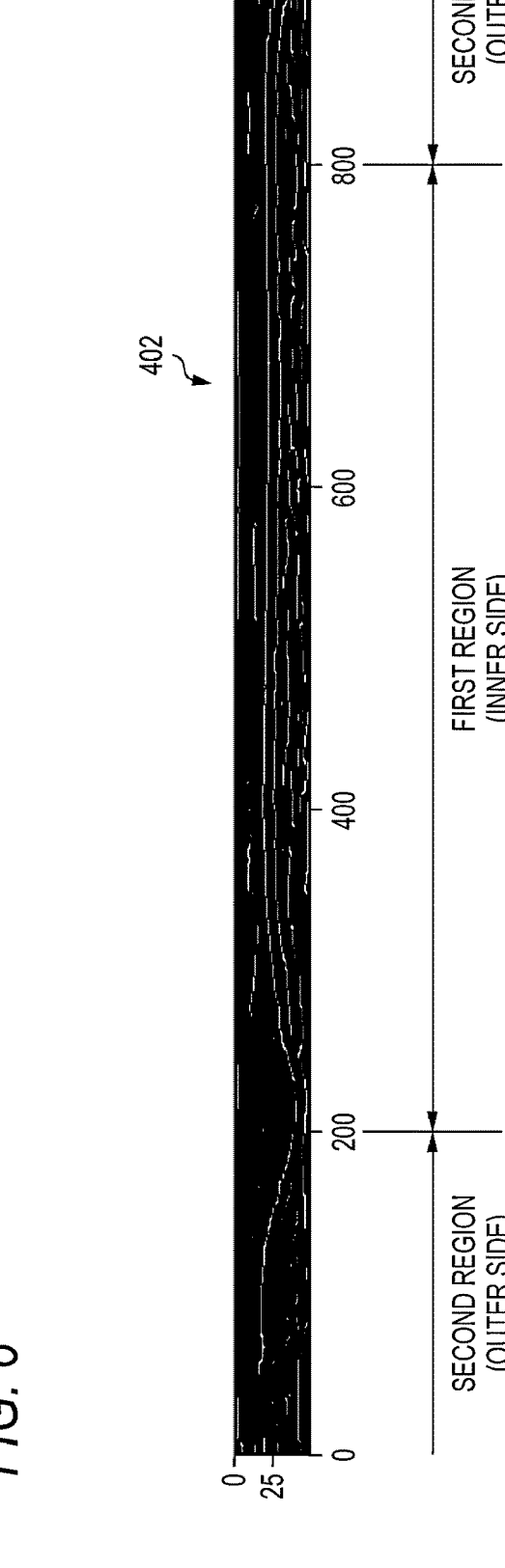
FIG. 6 is a diagram for explaining the inner side and the outer side of a region according to the illustrative embodiment of the present disclosure.

FIG. 6 is a flowchart illustrating details of the step S105 in FIG. 3.

Figure 4B:
FIG. 4B is a diagram for explaining the transition of an image to be processed according to the illustrative embodiment of the present disclosure.
Figure 4B:
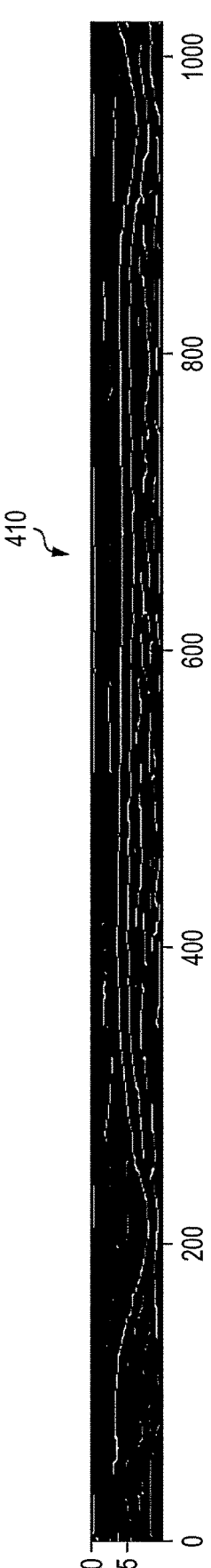

In step S201, the data processing unit 70 performs edge detection on the corneal image. Examples of the edge detection method include, but are not limited to, the Canny Edge detection, which is a known technique. For example, a corneal image 402 including a plurality of edges as illustrated in FIG. 4B is obtained as a result of performing the edge detection on the corneal image 401 illustrated in FIG. 4A.

In step S202, the data processing unit 70 performs region division on the corneal image obtained in step S201. In the present illustrative embodiment, the corneal image is divided into a first region on the center side (inner side) of the cornea and a second region on the sclera side (outer side) of the cornea. FIG. 6 illustrates an example in which the corneal image 402 illustrated in FIG. 4B is divided into a first region and a second region. Here, with the left end of the corneal image as a reference, the range of 0 to 200 pixels and 800 to 1024 pixels in the horizontal direction is treated as the second region, and the range of 201 to 799 pixels is treated as the first region. The dividing method here is an example, and is not limited thereto. For example, the range may be changed according to the size of the image. In addition, an example illustrated here is divided into two regions, but may be divided into more regions.

Figure 7A:
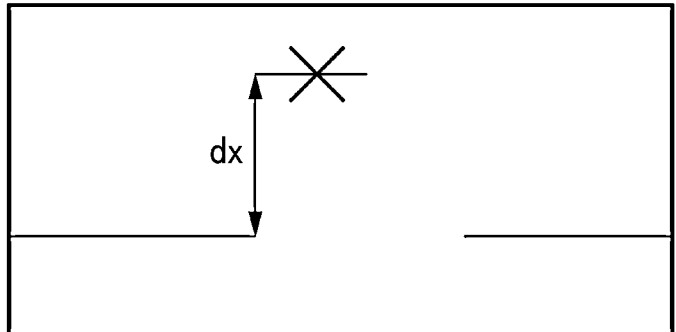
FIG. 7A is a diagram for explaining the edge joining conditions according to the illustrative embodiment of the present disclosure.
Figure 7B:
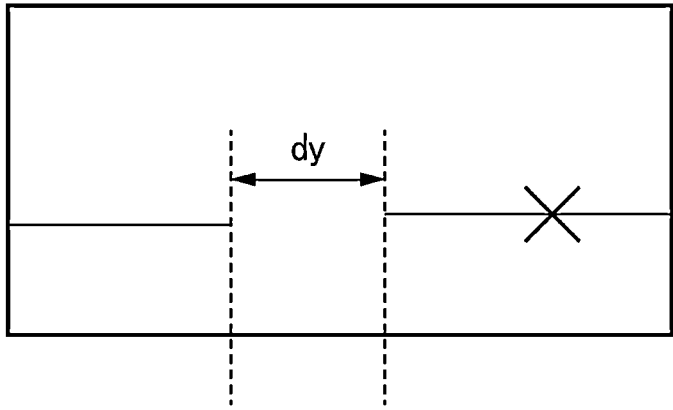
FIG. 7B is a diagram for explaining the edge joining conditions according to the illustrative embodiment of the present disclosure.
Figure 7C:
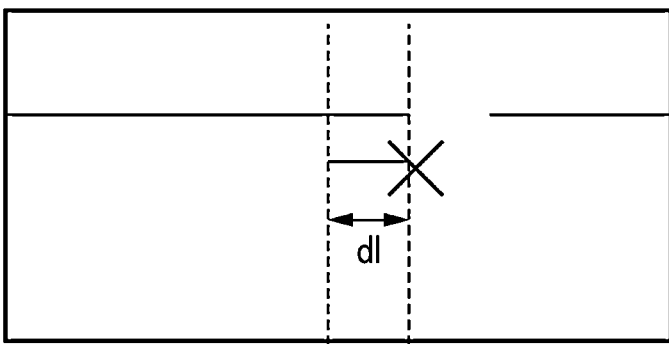
FIG. 7C is a diagram for explaining the edge joining conditions according to the illustrative embodiment of the present disclosure.

In step S203, the data processing unit 70 performs joining between edges on various edges included in the first region. FIGS. 7A to 7C are diagrams for explaining the conditions for edge joining. Here, the vertical direction (that is, corresponding to the thickness direction of the cornea) is defined as the x direction, and the horizontal direction (that is, corresponding to the width direction of the cornea) is defined as the y direction. FIG. 7A illustrates that the joining is not performed if the distance dx in the x direction between the closer end points of the two edges is a predetermined value or more. That is, the end points are joined by a straight line between the two edges if the distance dx between the two edges is smaller than the predetermined value. Similarly, FIG. 7B illustrates that the joining is not performed if the distance dy in the y direction between the closer end points of the two edges is a predetermined value or more. That is, the end points are joined by a straight line between the two edges if the distance dy between the edges is smaller than the predetermined value. FIG. 7C illustrates that, if two edges overlap in the x direction, the joining is not performed if the length d1 of the overlap is a predetermined value or more. That is, the end points are joined by a straight line between the two edges if the length d1 of the overlap of the edges is smaller than the predetermined value. At this time, the joining may be performed by smoothing or another joining process. In addition, in the case of joining edges partially overlapping in the vertical direction, the edge on the upper side (that is, the anterior side of the cornea) in the overlapping portion may be joined preferentially.

In the above example, a method of joining using three conditions has been described, but joining may be performed using any one of these conditions, or joining may be performed using other conditions. Further, the condition to be preferentially applied among the three conditions is not particularly limited. Here, the processing is repeated focusing on two edges whose end points are closest to each other. For convenience, the thresholds of the conditions used in step S203 are represented as $Th_{dx1}$, $Th_{dy1}$, and $T_{dl1}$.

In step S204, the data processing unit 70 removes edges based on the length and the intensity in the first region after the process of step S203. Among the edges included in the first region, the edges having a length equal to or less than the threshold $Th_{l1}$ are removed. In addition, among the edges included in the first region, the edges in which the maximum intensity of the pixels constituting the edge is equal to or less than the threshold Thai are removed. The threshold $Th_{l1}$ and the threshold $Th_{d1}$ used here are defined in advance and held in the storage device. Here, the length may be defined for each of the vertical direction and the horizontal direction, or may be defined by the number of pixels. The intensity may be defined by the pixel value (for example, the luminance value). In this step, the edges are removed based on both the length and the intensity, but the edges may be removed based on either one. By performing such edge removal, it is possible to remove the edges that are clearly not a boundary (the edges having low accuracy as a boundary), thereby improving the detection accuracy and improving the efficiency of the edge joining in the subsequent processes.

In step S205, similar to step S203, the data processing unit 70 performs the edge joining again in the first region subjected to the edge removal in step S204. The difference from step S203 is that the thresholds used as the joining conditions are made different. The thresholds of the conditions used in step S205 are represented as $Th_{dx2}$, $Th_{dy2}$, and $Th_{dl2}$. In this case, $Th_{dx2} > Th_{dx1}$, $Th_{dy2} > Th_{dy1}$, and $Th_{dl2} > Th_{dl1}$. That is, in step S205, the edges farther away from each other are also treated as the objects to be joined.

In step S206, the data processing unit 70 identifies the longest edge as a first edge and the second longest edge as a second edge among the edges included in the first region after the process of step S205. The length here may be identified by the number of pixels constituting the edge, or may be identified based on the length in the horizontal direction in the image.

In step S207, the data processing unit 70 performs edge joining with reference to the first edge and the second edge in the first region after the process in step S205. The joining conditions here may be the same as those in step S203, but the thresholds at the time of joining are made different. The thresholds of the conditions used in step S207 are represented as $Th_{dx3}$, $Th_{dy3}$, and $Th_{dl3}$. In this case, $Th_{dx3} > Th_{dx2} > Th_{dx1}$, $Th_{dy3} > Th_{dy2} > Th_{dy1}$, and $Th_{dl3} > Th_{dl2} > Th_{dl1}$. That is, in step S207, the edges farther away from the end points of the first edge and the second edge are also treated as the objects to be joined. The first edge and the second edge may be joined as a result of this process.

In step S208, the data processing unit 70 determines whether the first edge and the second edge are joined in the process of step S207. If the first and second edges are joined (YES in step S208), the process of the data processing unit 70 proceeds to step S210. On the other hand, if the first and second edges are not joined (NO in step S208), the process of the data processing unit 70 proceeds to step S209.

In step S209, the data processing unit 70 performs noise determination on the shorter edge of the two edges that are not joined based on the first edge and the second edge. That is, the longer one of the two edges is treated an edge more reliable as a boundary. The noise determination here is performed based on the distance between the two edges in the vertical direction. If the vertical distance is smaller than a predetermined threshold $Th_{dx4}$, the data processing unit 70 determines that the shorter edge is noise. The threshold $Th_{dx4}$ is defined in advance and held in the storage device.

In step S210, the data processing unit 70 identifies one or two reference edges. More specifically, if the first edge and the second edge are joined or if one is determined as noise, the longer edge is identified as the reference edge. On the other hand, if the first edge and the second edge are not joined and neither is determined as noise, the two edges are identified as the reference edges.

In step S211, the data processing unit 70 performs edge removal in the second region with reference to the positions of the one or two reference edges identified in step S210. Here, the edges of a predetermined threshold or more are removed based on the distance in the horizontal direction and the vertical direction and the degree of overlap based on the position of the reference edge. Further, in the second region, the edges having a length equal to or less than the threshold $Th_{l2}$ are removed. In addition, in the second region, the edges in which the maximum intensity of the pixels constituting the edge is equal to or less than the threshold $Th_{d2}$ are removed. The threshold $Th_{l2}$ and the threshold $Th_{d2}$ used here are defined in advance and held in the storage device. Here, the length may be defined for each of the vertical direction and the horizontal direction, or may be defined by the number of pixels. The intensity may be defined by the pixel value (for example, the luminance value). The threshold $Th_{l2}$ and the threshold $Th_{a2}$ used in this step may be the same as or different from the threshold $Th_{l1}$ and the threshold $Th_{a1}$ used for edge removal of the first region in step S204. In this step, the edges are removed based on both the length and the intensity, but the edges may be removed based on either one. By using the position of the reference edge as a reference, it is possible to efficiently remove the edges having low accuracy of the boundary, reduce the processing load of the edge joining in the subsequent processes, and shorten the processing time.

In step S212, the data processing unit 70 performs edge joining in the second region after the edge removal processing in step S211 with reference to the one or two reference edges identified in step S210. The joining conditions here may be the same as those in steps S203 and S205.

In step S213, the data processing unit 70 identifies one edge from among the edges after the edge joining in step S212. In this state, the corneal image includes one or two edges based on the one or two reference edges. At this time, if only one edge can be identified, the edge is identified. On the other hand, if two edges are included, if the edges overlap in the vertical direction, the edge located on the upper side, that is, on the anterior surface side of the cornea is identified. If the edges do not overlap each other in the vertical direction, the closer end points of the edges are joined by a straight line to form one edge, and the edge is identified.

In step S214, the data processing unit 70 performs smoothing on the edge identified in step S213. The smoothing may use a known method and is not particularly limited, but is adjusted such that the uneven portion as illustrated in the region 204 of FIG. 2 is not corrected excessively.

Figure 4C:
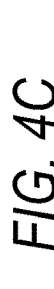
FIG. 4C is a diagram for explaining the transition of an image to be processed according to the illustrative embodiment of the present disclosure.
Figure 4C:
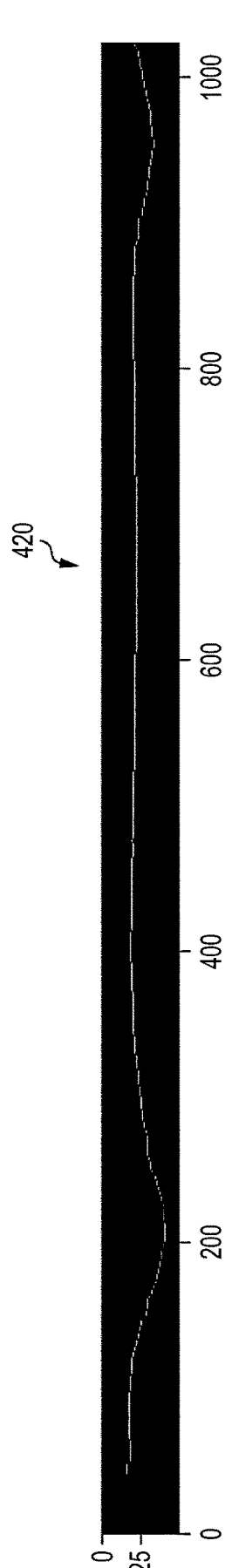

In step S215, the data processing unit 70 identifies the edge subjected to the smoothing in step S214 as the boundary of the Bowman's membrane. FIG. 4C is a corneal image 420 illustrating the boundary of the Bowman's membrane identified by the process up to here.

In step S216, the data processing unit 70 associates the position (coordinates) of the boundary identified in step S215 in the corneal image with the original OCT data. At this time, the coordinates and the like are associated based on the respective processing parameters of the boundary detection (step S102), the alignment (step S103), and the boundary extraction (step S104) of the corneal epithelium in FIG. 3. Then, this processing flow ends and proceeds to step S106 in FIG. 3.

Improvement of Artifacts

Figure 8A:
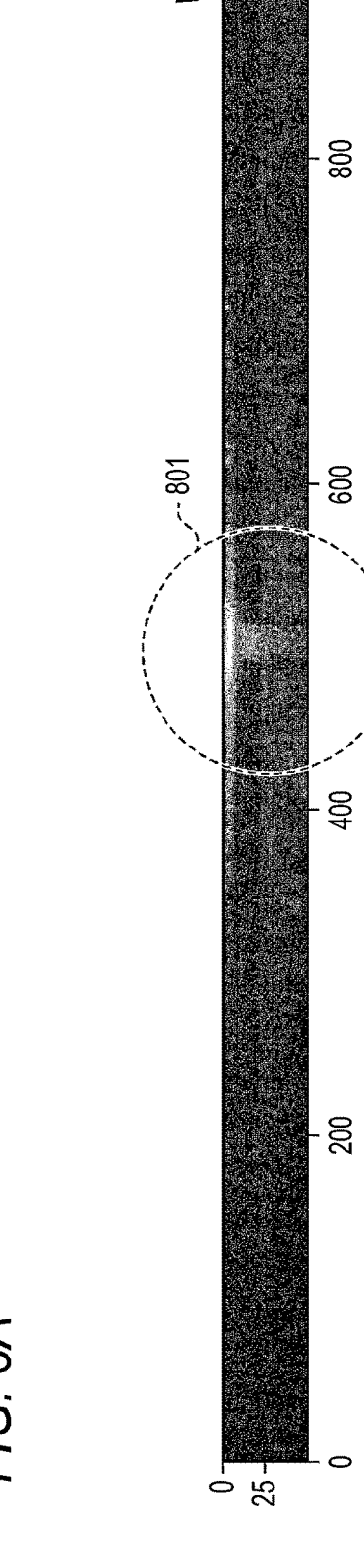
FIG. 8A is a diagram for explaining the improvement of artifacts generated in an OCT image.
Figure 8B:
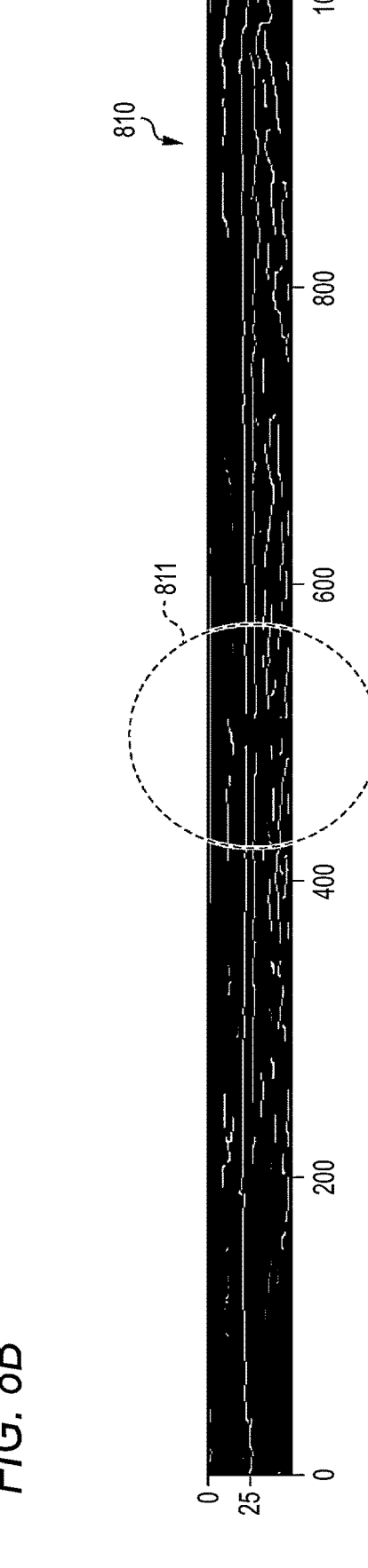
FIG. 8B is a diagram for explaining the improvement of artifacts generated in an OCT image.
Figure 8C:
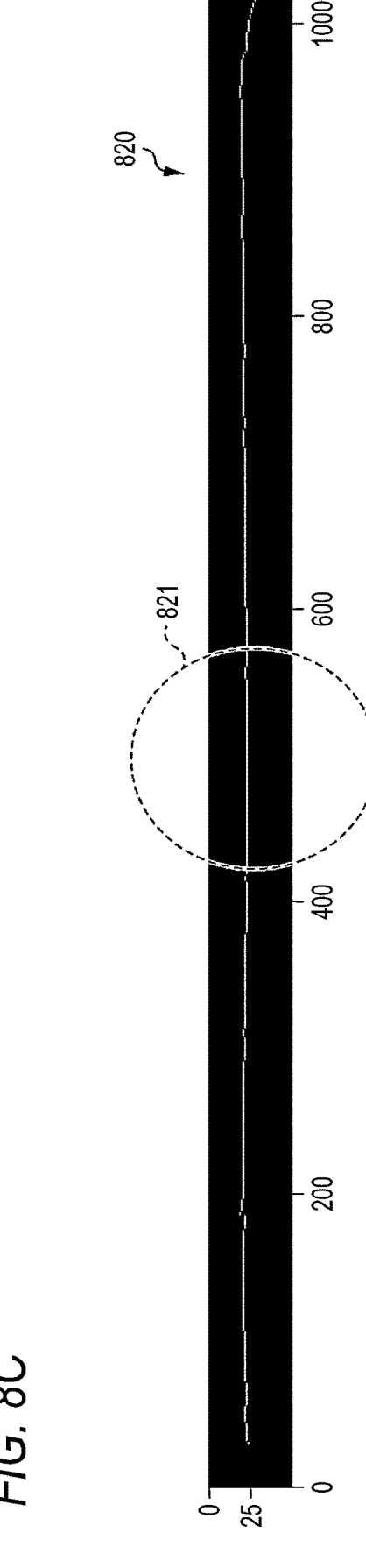
FIG. 8C is a diagram for explaining the improvement of artifacts generated in an OCT image.

FIGS. 8A to 8C are diagrams for explaining artifacts generated when OCT measurement is performed. A corneal image 800 as illustrated in FIG. 8A may be obtained as a result of the OCT measurement of the subject eye. At this time, a strong vertical artifact may occur at a position corresponding to the corneal apex as illustrated in a region 801. Such artifacts can be caused by the reflection from a portion perpendicular to the incident light during OCT measurement. When the analysis of the image including the artifact proceeds, the edge of the region 811 where the artifact is located cannot be appropriately detected as in the corneal image 810 illustrated in FIG. 8B. As a result, the distance between the edges to be detected is increased. This distance varies depending on the imaging conditions. Therefore, it is difficult to define the correction parameters and the like in advance in consideration of all the imaging conditions. In addition, if the conditions are not set appropriately, noise or the like is included excessively, and the detection accuracy is lowered.

However, in the anterior segment analysis method according to the present disclosure, as described above, two edges having a long length (the first edge and the second edge) are identified, and the boundary is detected based on these edges. Therefore, for example, even if an artifact is included as in the corneal image 800 of FIG. 8A, the edge joining can be performed appropriately in the region 821 where the artifact is located and one edge can be identified as illustrated in FIG. 8C.

Display Screen

An example of a display screen based on the analysis result obtained by the anterior segment analysis method according to the present illustrative embodiment will be described. The display screen described below is displayed on the UI unit 110, for example.

Figure 9A:
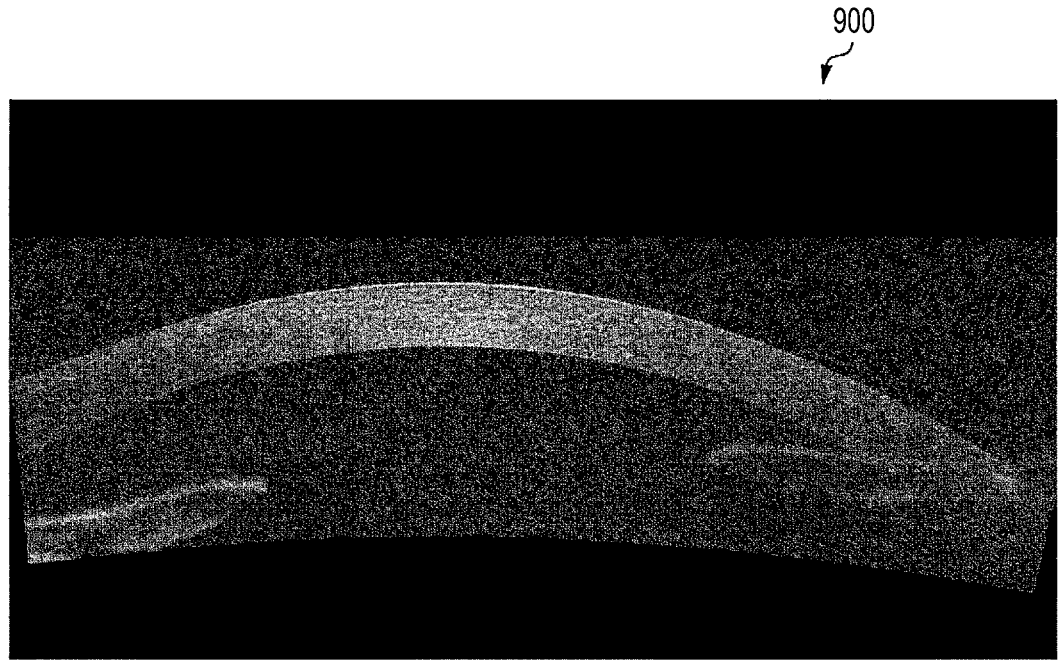
FIG. 9A is a display example illustrating the analysis result according to the illustrative embodiment of the present disclosure.
Figure 9B:
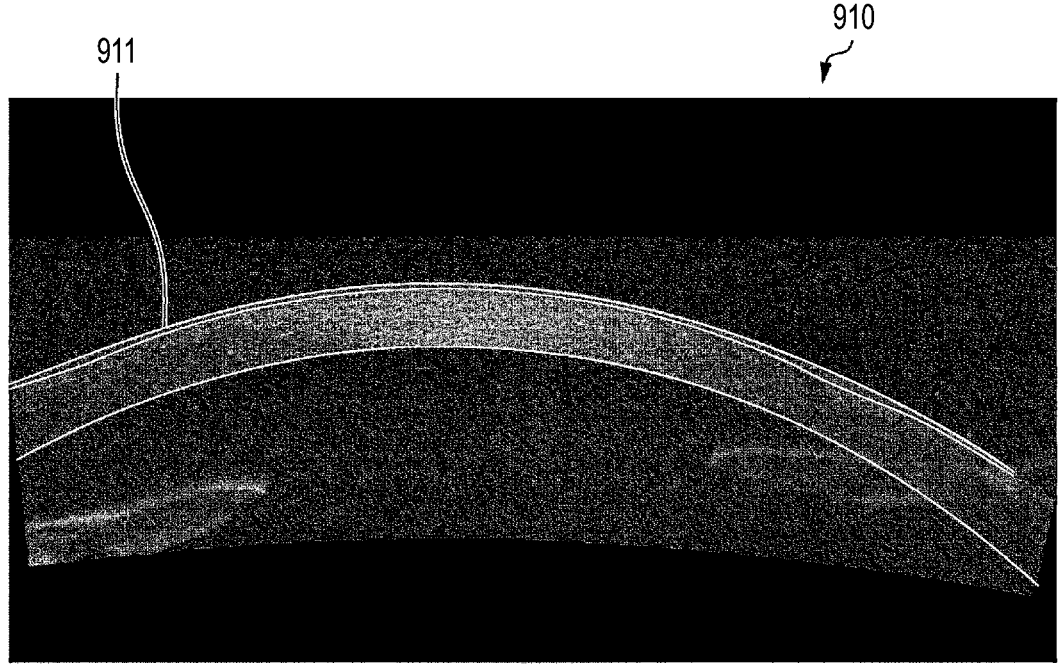
FIG. 9B is a display example illustrating the analysis result according to the illustrative embodiment of the present disclosure.

FIGS. 9A and 9B illustrate an example of a display screen on which the detected boundary is displayed in a manner superimposed on the OCT data. FIG. 9A illustrates an example of OCT data 900 obtained as a result of performing OCT measurement on the cornea. FIG. 9B is an example of a display image 910 in which each boundary is detected by applying the anterior segment analysis method according to the present illustrative embodiment to the OCT data 900 and displayed in a superimposed manner. The display image 910 illustrates three boundaries, including, in order from the top, the boundary on the anterior side of the corneal epithelium, the boundary between the corneal epithelium and the Bowman's membrane, and the boundary on the fundus side of the corneal endothelium.

In the display screen, the OCT data as illustrated in FIG. 9A and the display screen as illustrated in FIG. 9B may be switchable, or may be displayed in parallel. The display method of the detected boundary is not particularly limited, and for example, the line type and the line color may be switchable.

Figure 10:
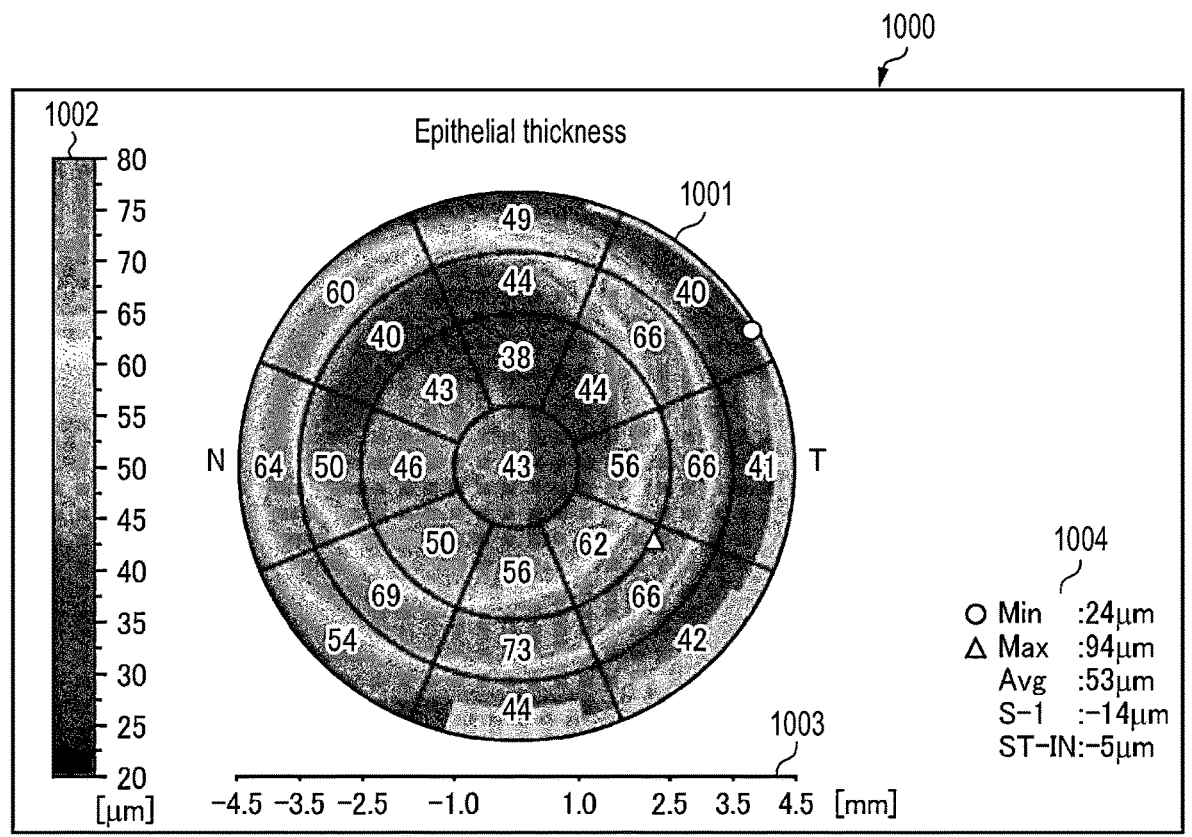
FIG. 10 is a diagram illustrating a display example of the analysis result according to the illustrative embodiment of the present disclosure.

FIG. 10 illustrates an example of a display screen 1000 for illustrating the thickness of the membrane derived based on the boundary obtained by the anterior segment analysis according to the present disclosure. Here, the boundary is identified and the thickness of the corneal epithelium in the entire cornea is derived by performing anterior segment analysis on each of a plurality of pieces of OCT data obtained by performing OCT scans a plurality of times on the subject eye. The thickness of the corneal epithelium corresponds to, for example, the distance from the boundary on the anterior side of the corneal epithelium to the boundary between the corneal epithelium and the Bowman's membrane. The thickness may be identified based on the length per pixel in the OCT data. When the thickness map indicating the thickness of the entire cornea is derived, the thickness is derived from a boundary obtained from each of a plurality of pieces of OCT data (for example, 12 pieces of OCT data obtained by radial scanning) to generate a sparse thickness map. Further, a dense thickness map may be generated by linear interpolation or the like from the thickness of each position on the cornea corresponding to each of the plurality pieces of OCT data. The interpolation method is not limited to linear interpolation, and may be other methods.

The number of measurements, the measurement direction, and the like are not particularly limited in the plurality of OCT measurements when measuring the cornea. For example, the OCT data may be obtained by performing radial scanning while rotating at every predetermined angle with the corneal center as the rotation axis. Alternatively, the OCT data may be obtained by performing a plurality of raster scans in parallel in a predetermined direction (for example, the upper-lower direction). Alternatively, the OCT data may be obtained based on the various scan patterns as described above.

The thickness map 1001 illustrates the entire region of the cornea, and illustrates the thickness of the corneal epithelium in the cornea by gradation. Here, an example in which the cornea is divided into 25 regions is illustrated, but the number of divided regions is not particularly limited. The numerical value illustrated in each region indicates the average value of the thickness in the region. The "N" illustrated on the left side of the thickness map 1001 indicates the nose side of the subject eye, and the "T" illustrated on the right side of the thickness map 1001 indicates the ear side of the subject eye.

The scale 1002 indicates the value of the thickness corresponding to the gradation indicated by the thickness map 1001. Here, the thickness is illustrated in a range of 20 to 80 [μm]. The scale 1002 indicates the length of the thickness map 1001 in the horizontal direction, and indicates a range of −4.5 to 4.5 [mm] with the center of the cornea as 0. A parameter group 1004 indicates the values of various parameters corresponding to the thickness map 1001. Illustrated here are the minimum value (Min) of the thickness, the maximum value (Max) of the thickness, the average value (Avg) of the entire thickness, the difference (S–I) between the average values of the thicknesses of the upper region and the lower region, and the difference (ST–IN) between the average values of the thicknesses of the upper region of T (ear) and the lower region of N (nose). A circular icon corresponding to the minimum value of the thickness and a triangular icon corresponding to the maximum value of the thickness are illustrated in the thickness map 1001, and indicate respective detection positions.

The contents and the configuration displayed on the display screen 1000 are examples, and other configurations may be used. For example, five parameters are illustrated in the parameter group 1004, but the parameters to be displayed may be designated by the user. In addition, whether to display the numerical values on the thickness map 1001 may be switchable. Moreover, the thickness map 1001 corresponding to one subject eye is displayed in FIG. 10, but both eyes or a comparison (for example, past measurement results) may be displayed in parallel.

As described above, according to the present illustrative embodiment, it is possible to allow appropriate segmentation on local unevenness of a layer constituting the cornea in the anterior segment. In particular, as compared with the method using curve approximation, it is possible to identify the boundary more accurately, even if the unevenness generated at the boundary of the Bowman's membrane or the like is captured and the accuracy of the OCT measurement is low, such as the anterior segment portion.

Other Illustrative Embodiments

In the present disclosure, a program or an application for achieving the functions of the one or more illustrative embodiments described above may be supplied to a system or an apparatus using a network, a storage medium, or the like. One or more processors in a computer of the system or the apparatus may read and execute the program.

In this specification, "processor" means a general-purpose or dedicated circuit such as a central processing unit (CPU), a graphic processing unit (GPU), an application specific integrated circuit (ASIC), a programmable logic device (for example, a simple programmable logic device (SPLD), a complex programmable logic device (CPLD), or a field programmable gate array (FPGA).

Further, provided is a program for causing a computer to execute not only the method described above as an example but also a control method for controlling the above-described apparatus. Such a program can be stored in any computer-readable recording medium. Examples of the recording medium include a semi-conductor memory, an optical disk, a magneto-optical disk (CD-ROM/DVD-RAM/DVD-ROM/MO or the like), and a magnetic storage medium (hard disk/Floppy (registered trademark) disk/ZIP or the like). It is also possible to transmit and receive the program through a network such as the Internet or a LAN. Similarly, the operation of the apparatus may be controlled based on the processing result executed by a processing unit arranged on a network or a control instruction.

As described above, the present invention is not limited to the above-described illustrative embodiment, and any modification, application, omission, or addition by a person skilled in the art based on the combination of the respective configurations of the illustrative embodiment, the description of the specification, and a well-known technique is also expected to be made by the present invention, and is included in the scope for which protection is sought.

As described above, the following matters are disclosed in the present specification.

(1) An anterior segment analysis apparatus (for example, the ophthalmic system 1, the control processing unit 50) including:

an obtainment unit (for example, the image forming unit 60) configured to obtain a tomographic image of an anterior segment including a cornea of a subject eye formed by OCT measurement;

a detection unit (for example, the data processing unit 70) configured to detect a plurality of edges included in the tomographic image;

a first joining unit (for example, the data processing unit 70) configured to perform joining between edges for each of the plurality of edges based on a first joining condition;

a selection unit (for example, the data processing unit 70) configured to select a first edge and a second edge from among the edges joined by the first joining unit based on a length;

a second joining unit (for example, the data processing unit 70) configured to perform joining between edges with reference to each of the first edge and the second edge based on a second joining condition; and a determination unit (for example, the data processing unit 70) configured to determine a boundary of a layer of the cornea of the tomographic image using the edges joined by the second joining unit.

According to this configuration, it is possible to allow appropriate segmentation on the local unevenness of a layer constituting the cornea in the anterior segment. In particular, it is possible to accurately detect the unevenness of the Bowman's membrane even if the imaging of the anterior segment is unclear in the OCT measurement.

(2) The anterior segment analysis apparatus according to (1), in which the detection unit is configured to:

identify an anterior boundary of a corneal epithelium in the tomographic image; and detect the plurality of edges in a predetermined range from the identified anterior boundary.

According to this configuration, by detecting the plurality of layers constituting the cornea in a predetermined range, it is possible to reduce the processing load related to the detection of the boundary and efficiently detect the boundary.

(3) The anterior segment analysis apparatus according to (1) or (2), in which the tomographic image is divided into a first region, which is a region on a corneal apex side of the subject eye, and a second region, which is a region on a sclera side of the cornea of the subject eye, in which the first joining unit processes the first region, and in which the second joining unit processes the first region and the second region.

According to this configuration, the cornea apex side is detected with higher accuracy, and the outside is detected based on the result. Accordingly, the processing load related to the detection of the boundary can be reduced and the boundary can be efficiently detected without lowering the detection accuracy of the entire region for detecting the boundary.

(4) The anterior segment analysis apparatus according to (3), in which the second joining unit makes a joining condition for joining edges in the first region and a joining condition for joining edges in the second region different from each other.

According to this configuration, the processing load related to the detection of the boundary can be reduced and the boundary can be efficiently detected without lowering the detection accuracy of the entire region for detecting the boundary. In particular, the edge can be detected more efficiently in the second region.

(5) The anterior segment analysis apparatus according to (3) or (4), in which in a case where the first edge and the second edge overlap each other by a predetermined length or more in a width direction of the cornea in the first region, the second joining unit determines a longer one of the first edge and the second edge as the boundary of the layer of the cornea.

According to this configuration, it is possible to efficiently identify an edge having a higher probability of being a boundary based on the length.

(6) The anterior segment analysis apparatus according to any one of (3) to (5), in which in a case where the first edge and the second edge do not overlap each other in a width direction of the cornea in the first region, the second joining unit joins the first edge and the second edge and determines the joined first edge and second edge as the boundary of the layer of the cornea.

According to this configuration, even if the edges included in the OCT image are broken in the width direction, it is possible to appropriately join the edges and identify the boundary by interpolating between the edges.

(7) The anterior segment analysis apparatus according to (6), in which in a case where the first edge and the second edge do not overlap each other in the width direction of the cornea in a range defined based on an imaging condition of the OCT measurement in the first region, the second joining unit joins the first edge and the second edge and determines the joined first edge and second edge as the boundary of the layer of the cornea.

According to this configuration, even if a position such as the corneal apex in the OCT image includes an artifact and the edge cannot be extracted at the artifact, the edge can be interpolated and the boundary can be identified accurately.

(8) The anterior segment analysis apparatus according to any one of (1) to (7), in which the first joining condition and the second joining condition are different from each other in at least one of a distance in a thickness direction of the cornea, a distance in a width direction of the cornea, a degree of overlap in the width direction of the cornea, or an edge intensity when joining edges.

According to this configuration, by joining the plurality of edges included in the OCT image using the plurality of joining conditions, it is possible to appropriately join the edges and identify the boundary.

(9) The anterior segment analysis apparatus according to any one of (1) to (8), in which the second joining unit further performs smoothing on the joined edges.

According to this configuration, even if unevenness such as a step is generated at the time of the edge joining, it is possible to perform adjustment by smoothing to approach the actual boundary.

(10) The anterior segment analysis apparatus according to any one of (1) to (9), further including:

a display control unit (for example, the data processing unit 70) configured to display the boundary of the layer of the cornea determined by the determination unit in a manner superimposed on the tomographic image and identifiable.

According to this configuration, the user of the ophthalmic system can easily grasp the detected layered structure of the cornea, which can promote the efficiency in diagnosis or the like.

(11) The anterior segment analysis apparatus according to any one of (1) to (9), further including:

a derivation unit (for example, the data processing unit 70) configured to derive a thickness of a corneal epithelium of the subject eye based on the boundary determined by the determination unit; and a generation unit (for example, the data processing unit 70) configured to generate a thickness map of the corneal epithelium of the subject eye using the thickness derived by the derivation unit.

According to this configuration, the thickness with respect to the detected layered structure of the cornea can be expressed more visually, which can improve the convenience of the user of the ophthalmic system.

(12) An anterior segment analysis method including:

an obtainment step (for example, step S101) of obtaining a tomographic image of an anterior segment including a cornea of a subject eye formed by OCT measurement;

a detection step (for example, step S201) of detecting a plurality of edges included in the tomographic image;

a first joining step (for example, step S203, step S205) of performing joining between edges for each of the plurality of edges based on a first joining condition;

a selection step (for example, step S206) of selecting a first edge and a second edge from among the edges joined by the first joining step based on a length;

a second joining step (for example, step S212) of performing joining between edges with reference to each of the first edge and the second edge based on a second joining condition; and a determination step (for example, step S213, step S215) of determining a boundary of a layer of the cornea of the tomographic image using the edges joined by the second joining step.

According to this configuration, it is possible to allow appropriate segmentation on the local unevenness of a layer constituting the cornea in the anterior segment. In particular, it is possible to accurately detect the unevenness of the Bowman's membrane even if the imaging of the anterior segment is unclear in the OCT measurement.

(13) A program for causing a computer (for example, the ophthalmic system 1) to perform:

an obtainment step (for example, step S101) of obtaining a tomographic image of an anterior segment including a cornea of a subject eye formed by OCT measurement;

a detection step (for example, step S201) of detecting a plurality of edges included in the tomographic image;

a first joining step (for example, step S203, step S205) of performing joining between edges for each of the plurality of edges based on a first joining condition;

a selection step (for example, step S206) of selecting a first edge and a second edge from among the edges joined by the first joining step based on a length;

a second joining step (for example, step S212) of performing joining between edges with reference to each of the first edge and the second edge based on a second joining condition; and a determination step (for example, step S213, step S215) of determining a boundary of a layer of the cornea of the anterior segment using the edges joined by the second joining step.

According to this configuration, it is possible to allow appropriate segmentation on the local unevenness of a layer constituting the cornea in the anterior segment. In particular, it is possible to accurately detect the unevenness of the Bowman's membrane even if the imaging of the anterior segment is unclear in the OCT measurement.

Although various illustrative embodiments have been described above with reference to the drawings, the present invention is not limited to these examples. It is apparent to those skilled in the art that various modifications or modifications can be conceived within the scope described in the claims, and it is understood that the modifications or modifications naturally fall within the technical scope of the present invention. In addition, the components described in the above illustrative embodiments may be arbitrarily combined without departing from the purpose of the invention.

The present application is based on the Japanese patent application (Japanese Patent Application No. 2021-121653) filed on Jul. 26, 2021, and the contents thereof are incorporated herein by reference.

The invention claimed is:

1. An anterior segment analysis apparatus comprising:
a control device configured to:
obtain a tomographic image of an anterior segment including a cornea of a subject eye formed by OCT measurement;

detect a plurality of edges included in the tomographic image;

perform a first joining comprising joining between edges for each of the plurality of edges based on a first joining condition;

select a first edge and a second edge from among the edges joined by the first joining based on a length;

perform a second joining comprising joining between edges with reference to each of the first edge and the second edge based on a second joining condition; and determine a boundary of a layer of the cornea of the tomographic image using the edges joined by the second joining.

2. The anterior segment analysis apparatus according to claim 1, wherein the control device is further configured to:
identify an anterior boundary of a corneal epithelium in the tomographic image; and
detect the plurality of edges in a predetermined range from the identified anterior boundary.

3. The anterior segment analysis apparatus according to claim 1,
wherein the tomographic image is divided into a first region and a second region, the first region corresponding to a corneal apex side of the subject eye, the second region corresponding to a sclera side of the cornea of the subject eye,
wherein the control device performs the first joining on the first region, and
wherein the control device performs the second joining on the first region and the second region.

4. The anterior segment analysis apparatus according to claim 3, wherein in the performing of the second joining, the control device makes a joining condition for joining edges in the first region and a joining condition for joining edges in the second region different from each other.

5. The anterior segment analysis apparatus according to claim 3, wherein in the performing of the second joining, in a case where the first edge and the second edge overlap each other by a predetermined length or more in a width direction of the cornea in the first region, the control device determines a longer one of the first edge and the second edge as the boundary of the layer of the cornea.

6. The anterior segment analysis apparatus according to claim 3, wherein in the performing of the second joining, in a case where the first edge and the second edge do not overlap each other in a width direction of the cornea in the first region, the control device joins the first edge and the second edge and determines the joined first edge and second edge as the boundary of the layer of the cornea.

7. The anterior segment analysis apparatus according to claim 6, wherein in the performing of the second joining, in a case where the first edge and the second edge do not overlap each other in the width direction of the cornea in a range defined based on an imaging condition of the OCT measurement in the first region, the control device joins the first edge and the second edge and determines the joined first edge and second edge as the boundary of the layer of the cornea.

8. The anterior segment analysis apparatus according to claim 1, wherein the first joining condition and the second joining condition are different from each other in at least one of a distance in a thickness direction of the cornea, a distance in a width direction of the cornea, a degree of overlap in the width direction of the cornea, or an edge intensity when joining edges.

9. The anterior segment analysis apparatus according to claim 1, wherein in the performing of the second joining, the control device further performs smoothing on the joined edges.

10. The anterior segment analysis apparatus according to claim 1, wherein the control device is further configured to:
display the determined boundary of the layer of the cornea in a manner superimposed on the tomographic image and identifiable.

11. The anterior segment analysis apparatus according to claim 1, wherein the control device is further configured to:

derive a thickness of a corneal epithelium of the subject eye based on the determined boundary; and generate a thickness map of the corneal epithelium of the subject eye using the derived thickness.

12. An anterior segment analysis method comprising:

obtaining a tomographic image of an anterior segment including a cornea of a subject eye formed by OCT measurement;

detecting a plurality of edges included in the tomographic image;

performing a first joining comprising joining between edges for each of the plurality of edges based on a first joining condition;

selecting a first edge and a second edge from among the edges joined by the first joining based on a length;

performing a second joining comprising joining between edges with reference to each of the first edge and the second edge based on a second joining condition; and determining a boundary of a layer of the cornea of the tomographic image using the edges joined by the second joining.

13. A non-transitory computer-readable storage medium storing a computer program readable by a computer, the computer program, when executed by the computer, causing the computer to perform operations comprising:

obtaining a tomographic image of an anterior segment including a cornea of a subject eye formed by OCT measurement;

detecting a plurality of edges included in the tomographic image;

performing a first joining comprising joining between edges for each of the plurality of edges based on a first joining condition;

selecting a first edge and a second edge from among the edges joined by the first joining based on a length;

performing a second joining comprising joining between edges with reference to each of the first edge and the second edge based on a second joining condition; and determining a boundary of a layer of the cornea of the anterior segment using the edges joined by the second joining.

\* \* \* \* \*